(12) United States Patent
Kobayashi et al.

(10) Patent No.: US 6,214,371 B1
(45) Date of Patent: Apr. 10, 2001

(54) METHOD FOR BREEDING HIGHLY LACTIFEROUS COWS BY USING RUMEN-PROTECTIVE AMINO ACIDS

(75) Inventors: Hisamine Kobayashi; Hiroyuki Sato; Takeshi Fujieda, all of Kawasaki (JP); Hiroyuki Suzuki, Morrisonville, NY (US)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/147,578

(22) PCT Filed: Jul. 18, 1997

(86) PCT No.: PCT/JP97/02499

§ 371 Date: Feb. 24, 1999

§ 102(e) Date: Feb. 24, 1999

(87) PCT Pub. No.: WO98/04152

PCT Pub. Date: Feb. 5, 1998

(30) Foreign Application Priority Data

Jul. 26, 1996 (JP) .................................................. 8-197694

(51) Int. Cl.[7] .......................... A61K 9/14; A61K 31/195
(52) U.S. Cl. .......................... 424/438; 424/442; 514/556; 514/561; 514/562; 514/563; 514/564; 426/2; 426/807
(58) Field of Search ..................................... 424/438, 442, 424/484; 514/554, 556, 557, 561, 562, 563, 564, 578; 426/2, 89, 650, 807

(56) References Cited

U.S. PATENT DOCUMENTS

| | | | |
|---|---|---|---|
| 5,635,198 | * | 6/1997 | Nishimura et al. .................. 424/438 |
| 5,637,312 | * | 6/1997 | Tock et al. ........................... 424/438 |
| 5,720,970 | * | 2/1998 | Rode et al. ........................... 424/438 |
| 5,906,842 | * | 5/1999 | Sato et al. .................................. 426/2 |

FOREIGN PATENT DOCUMENTS

| | | | |
|---|---|---|---|
| 2-255047 | * | 10/1990 | (JP) . |
| 5-192093 | * | 8/1993 | (JP) . |
| 6-237701 | * | 8/1994 | (JP) . |
| 6-237702 | * | 8/1994 | (JP) . |
| 7-313068 | * | 12/1995 | (JP) . |

* cited by examiner

*Primary Examiner*—Neil D. Levy
(74) *Attorney, Agent, or Firm*—Oblon, Spivak, McClelland, Maier & Neustadt, P.C.

(57) ABSTRACT

Lysine and methionine which are limiting amino acids of dairy cows are administered to dairy cows to decrease the BUN value that has an adverse effect on the conception rate and to increase the blood glucose required to improve the energy balance, that alanine and glutamine are administered to dairy cows to increase the blood glucose and to improve the liver function, and that the use of these amino acids is effective for keeping good conditions of dairy cows, allowing earlier arrival of initial estrus without any stress, improving the mating conception rate and decreasing the non-conception rate.

12 Claims, No Drawings

US 6,214,371 B1

METHOD FOR BREEDING HIGHLY LACTIFEROUS COWS BY USING RUMEN-PROTECTIVE AMINO ACIDS

TECHNICAL FIELD

The present invention relates to a nutrient feed for expediting breeding of high-level lactation dairy cows and a method of breeding dairy cows by feeding them with the nutrient feed.

TECHNICAL BACKGROUND

Dairy cows rapidly increase amounts of their milk from immediately after calving to the prior period of lactation to recover their bodily strength in the puerperal period. Accordingly, the energy consumption of dairy cows reaches the maximum, and the nutrition demand is physiologically increased. Despite this, even normal healthy dairy cows reduce the appetite owing to their puerperium, and the feed intake is temporarily reduced. Consequently, although the energy and the nutrient are not sufficiently supplemented, the energy consumption is great, so that the energy balance becomes minus and the insufficient nutrition occurs. As a result, dairy cows naturally try to supply the energy upon using all of their body fats. Unless the metabolism in the body proceeds smoothly, ketosis or an abomasum displacement occurs. The energy is used preferentially in the order of body maintenance, lactation and breeding. When the energy balance is in the minus condition, it causes the decrease in the body weight of dairy cows, diseases and environmental stress, as well as the delay of the first estrus of dairy cows and the ovary function disorder thereof, influencing the breeding results (Mizomoto K., Dairy Japan, February 1993, extra edition).

Yasuho states that ruminants tend to suffer from abnormal metabolism of sugar and lipid, such as ketosis at the peak stage of lactation or at the final stage of conception (New Chemistry of Dairy Cows, Noson Gyoson Bunka Kyokai, published Jul. 15, 1987). He further states by citing Krebs (1996) that when glyconeogenesis increases in the liver, the formation of ketones increases.

In the diabetic complication that risks the life, ketones (D-3-hydroxybutyric acid, acetoacetic acid and acetone) are formed, and proton at a high concentration that exceeds an acid-base buffer system of the body is formed, resulting in the dangerous decrease in the pH of the blood. Although ketones have been considered to be metabolic wastes, it is currently known that ketones are used as a fuel in addition to ordinary fuel glucose of the brain in the fasting. The controlled formation of ketones induces ketosis. In the ketosis, the pH of the blood remains buffered in the normal range. This is quite an important glucose saving to the fasting. Since the brain cannot use fatty acid as a fuel, glycogen stored comes to be exhausted ("Easy Metabolism, Basic Knowledge of Nutrient Metabolism" translated by Aso Y.).

G. D. Baird (J. Dairy Sci. (65) 1–10, 1982) states that the increase in the concentration of ketones in the blood has an adverse effect on breeding of dairy cows.

Baalsrud (Nils-Ivar Baalsrud, U.S. Pat. No. 3,959,496) discloses that before or after calving of dairy cows, the actual amount of milk is not balanced with the amount of milk produced from the energy inherent in dairy cows and the actual amount of milk is increased from 1 month before calving to 5 months after calving, with the result that the energy balance of dairy cows is lost during this period, the consumption is increased and the overall energy balance is minus. It is further stated that a rumen-bypassed biologically active substance and glucose are administered to improve this.

Kato discloses that since excess intake of proteins in dairy cows in the peak period of lactation deprives the energy of dairy cows, the energy loss of dairy cows greatly influences the breeding, that a protein decomposed in a rumen becomes ammonia and is used by bacteria in the rumen but excess ammonia is detoxicated into urea in the liver which increases blood urea nitrogen (BUN), and that when the BUN value increases, a sperm, an egg and a fetus (embryo) are seriously influenced and killed (Kato H., Dairy Japan, February 1993, extra edition).

Butler studied a relationship between the BUN value and the conception rate in the first estrous period after 60 days from calving, and reported that the conception rate is 53% at the blood concentration of 19 mg/dl or less, whereas it is decreased to 35% at the blood concentration of more than 19 mg/dl (W. R. Butler et al., J. Anim. Sci. 1996, 74: 858–865).

Meijeijer measured a concentration of a free amino acid in the plasma and the muscle of high-level lactation dairy cows to which a concentrated feed, a corn silage and a predried hay silage were administered from 2 weeks before calving to 15 weeks after calving. As a result, it was found that the concentrations of methionine, phenylalanine, glutamic acid and glutamine in the plasma during the period of from 6 to 15 weeks after calving were reduced by from 16 to 25% as compared with those before calving. The change in the amino acid concentration in the muscle from the later stage of conception to the initial stage of lactation suggested that the protein in the muscle is decomposed because amino acids are supplied to a mammary gland. It is further stated that in the high-level lactation dairy cows, glutamine latently controls the synthesis of a milk protein [G. A. L. Meijeijer et al., J. Dairy Sci., 78, (S), 1131 (1995)].

Torii [Japanese Laid-Open (Kokai) No. 54,320/1988] discloses a pharmaceutical composition which is composed mainly of alanine and glutamine and which is effective for treating anti-alcoholic diseases. Mawatari [Japanese Laid-Open (Kokai) No. 229,940/1993] discloses hepatocyte regeneration accelerating agent which contains alanine or glutamine as an essential ingredient and which can increase hepatocytes to accelerate regeneration of the liver. Mawatari [Japanese Laid-Open (Kokai) No. 221,858/1993] discloses that a hepatitis treating agent containing at least one of alanine, glutamine and ornithine is effective for treating viral hepatitis, drug-induced hepatitis and fulminant hepatitis. Suda [Japanese Laid-Open (Kokai) No. 50,917/1986] discloses an anti-alcoholic liver disorder-treating composition containing alanine and ornithine as active ingredients.

The present invention is to develop a nutrient feed for expediting breeding of dairy cows and a method of expediting breeding of dairy cows by feeding them with the nutrient feed.

DISCLOSURE OF THE INVENTION

The present inventors have found that lysine and methionine which are limiting amino acids of dairy cows are administered to dairy cows to decrease the BUN value that has an adverse effect on the conception rate and to increase the blood glucose required to improve the energy balance, that alanine and glutamine are administered to dairy cows to increase the blood glucose and to improve the liver function, and that the use of these amino acids is effective for keeping good conditions of dairy cows, allowing earlier arrival of initial estrus without any stress, improving the mating conception rate and decreasing the non-conception rate. These findings have led to the completion of the present invention.

That is, the present invention relates to a dairy cow feed or a corn silage basic formula feed containing rumen-bypassed lysine (1) and glutamine and/or alanine (2) as essential ingredients and optionally containing methionine (3), and a method of breeding high-level lactation dairy cows, characterized in that a corn silage basic formula feed containing rumen-bypassed lysine (1) and glutamine and/or alanine (2) as essential ingredients and optionally methionine (3) is continuously administered to high-level lactation dairy cows from 21 days before calving, preferably from 3 days before calving to 84 days after calving such that the energy balance of high-level lactation dairy cows is always plus and at least the amino acid demand of high-level lactation dairy cows is satisfied.

In order that dairy cows lactate, raise embryos and maintain their own life, it is necessary to consider the minimum protein balance and energy balance. The protein balance is determined from the amount of protein (DP) required by dairy cows, the amount of protein (IP) fed to dairy cows by feed intake and through protozoa in a rumen and the amount of protein (RP) lost by scarves, urine, fecal matters and protozoa in a rumen. When these amounts are in the order of IP−RP>DP, the amounts of proteins of dairy cows are satisfied. However, when the amounts of proteins are considered in more detail from the standpoint of amino acids constituting proteins, the amino acid balance in the bodies of dairy cows is inconsistent with ratios of amino acids in proteins of dairy cows, and there are amino acids (limiting amino acids) in amounts which do not reach those required to constitute proteins. When these amino acids are supplied, the balance of amino acids required to constitute proteins is given as a whole, and proteins are effectively used. Thus, there is no amino acid loss.

Meanwhile, unless limiting amino acids are supplied, the synthesis of proteins in the bodies of dairy cows is restricted to the level of limiting amino acids. Since amino acids other than limiting amino acids which do not constitute proteins are not used as proteins, these proteins are, in many cases, metabolized or exhausted outside bodies through various routes. During this metabolism, the increase in the BUN value of the blood is observed, and it shows a great burden on the liver function of dairy cows. Further, the increase in the BUN value of the blood has an adverse effect on the conception rate of dairy cows, and gives various influences such as the decrease in the bodily strength of dairy cows, the delay of recovery thereof and the like.

Accordingly, all of amino acids effectively function to form proteins within dairy cows by supplying limiting amino acids to the level of amino acids constituting proteins. As a result, the presence of extra amino acids that do not constitute proteins come to be extremely suppressed. Therefore, ideally, until amino acids which dairy cows have to exhaust outside their bodies through metabolism disappear, the BUN value of the blood derived from these amino acids is not increased, nor is a burden exerted on the liver function ot dairy cows.

However, the body conditions of dairy cows are actually not constant, but always changed.

The BUN value of the blood cannot be reduced to zero because of the irregularity of feed ingredients, the change in the feed intake, the change in digestion and absorption of feed, and the ability of dairy cows themselves to synthesize proteins. Further, when the BUN value of the blood is high, the burden of the liver is increased owing to excess intake of proteins, imbalance of amino acids and the like. Accordingly, it is important that the liver function of dairy cows is always kept good and dairy cows are controlled not to undergo the liver function disorder. The present inventors have found that alanine and/or glutamine is effective for improving the liver function of dairy cows. The administration of alanine and/or glutamine helps to keep good the liver function and the health conditions of dairy cows.

The types of limiting amino acids and the insufficient amounts thereof can be determined upon calculating necessary amounts of amino acids of a ruminant and amounts of amino acids given from a feed. In this calculation, a Cornell model on a carbohydrate and a protein system for determination of a feed of dairy cows is known (Search: Agriculture Ithaca, NY: Cornell Univ. Agr. Exp. No. 34, 128 pp. 1990, ISSN 0362-2754, cited herein as a reference data). This is proposed, as a model for estimation of an amino acid demand or a feed of dairy cows and for calculation of various changes with respect to adjustment of necessary amounts of nutrients of dairy cows which are changed over the course of time, formulation of a feed based thereon, control of proliferation of dairy cows, control of breeding, environmental influence through inhibition of excreta of dairy cows and the like. This model is applicable to a computer spread sheet, and can be used in both beef cattle and dairy cows in different levels and different production types. The Cornell model makes it possible to calculate metabolic proteins of dairy cows based on the type, the body weight in birth, the overall body weight and the like under specific conditions of individual dairy cows (namely, whether dairy cows are in the maintenance cycle or in the lactation period or in the breeding period). Further, in this model, it is considered that dairy cows are reactive with a feed supplied on the basis of a feed composition, a digestion rate and digestive proteins (digestive proteins which are not influenced by the function of the forestomach and proteins of bacteria digested). Metabolic proteins required by a specific ruminant are calculated in this manner, and the amounts of these proteins are compared with calculated amounts of metabolic proteins given from a feed supplied. When feeding digestive proteins in amounts less than those required for specific dairy cows in consideration of the physiological condition and the lactation period, a feed additive containing the above-mentioned rumen-bypassed amino acids of dairy cows comes to be supplied to a necessary level.

The amount of the feed additive of rumen-bypassed amino acids added to the basic feed is calculated by replacing the amounts of digestive proteins lacking in the feed with amounts of methionine and/or lysine protected from the function of the forestomach. This replacement can be conducted by analyzing amino acids of digestive proteins (supplied from the feed) using the above-mentioned Cornell model proposed by Chalupa et al. (Cornell Conference for production of a feed in 1991, p. 44, cited herein as a reference data). A protein fraction of a feed which has been decomposed in the first (rumen) through third (psalterium) stomachs of dairy cows is first separated from a protein fraction which has not been decomposed in the forestomachs, and the amounts of methionine and lysine required for lactation and maintenance which amounts are calculated using the Cornell model are totalled, making it possible to calculate the amounts of methionine and lysine required for a specific ruminant.

The types of essential amino acids to dairy cows and the insufficient amounts thereof to dairy cows can be known in detail from the above-mentioned analyses including computer models other than the above-mentioned model. However, these amounts are calculated amounts, and might be sometimes inconsistent with actual amounts. For example, dairy cows consume their bodily strength in calving. Consequently, the bodily strength is decreased immediately after calving, and the feed intake is reduced by approximately 20% on the average. When dairy cows are bred and the amount of their milk, the quality of milk and their health conditions are observed, the ideal breeding procedure obtained from the computer model is not actually shown. However, even in this state, the amount of milk is actually as expected, and the quality of milk is not extremely decreased. This means that dairy cows themselves try instinctively to continuously produce a necessary amount of milk during the lactation period. Consequently, dairy cows are under serious bodily burden, experience various stresses and consume their bodily strength. This influences the production of milk in the following years, and also causes the increase in the stress of dairy cows, the delay of the first estrus, the ovary function disorder and the decrease in the conception rate. As a result, the number in days of non-conception is increased, and the economical loss is great to dairy farmers.

Alanine and glutamine are also important to dairy cows, though these are not amino acids other than the essential amino acids to dairy cows according to the above-mentioned computer model. These amino acids increase blood glucose which is a basic energy to dairy cows, and help dairy cows eliminate the decrease in the bodily strength and the stress owing to calving, making it possible to maintain the good health conditions.

The above-mentioned amino acids improve the liver function. Accordingly, even when dairy cows undergo a burden in the liver for some reasons, the intake of these amino acids can return the liver function to a normal state.

Consequently, the combined use of lysine, methionine, alanine and glutamine can maintain the good conditions of dairy cows as a whole. Specifically, the BUN value of the blood is decreased, and the blood glucose value is increased to maintain the liver function. When the disorder of the liver occurs, it is eliminated. Therefore, when the preferable conditions of maintaining the preferable health conditions of dairy cows are satisfied as mentioned above, good results of breeding are given, and preferable economical effects to dairy farmers, such as earlier arrival of the first estrus, the decrease in the number of matings and the decrease in the non-conception rate can be brought forth.

EXAMPLES

The present invention is illustrated specifically by referring to the following Examples.

Production Example 1

Production Example of rumen-bypass amino acid:

L-lysine hydrochloride (325 g), 99.5 g of methionine, 250 g of alanine, 250 g of glutamine, 172.5 g of talc, 2.5 g of sodium carboxymethylcellulose and 135 g of water were charged into a kneader, and kneaded. The mixture was formed into cylindrical granules using an extrusion-pulverizer having a screen with 1.5 mm φ openings. The shape of the thus-obtained granules was adjusted using a device for forming spherical granules (Malmerizer, supplied by Fuji Paudal) to obtain nearly spherical granules. The resulting spherical granules were subjected to fluidized drying to give cores containing L-lysine hydrochloride and having a diameter distribution of from 1 mm to 2.5 mm.

A protective substance containing 1.68 parts by weight of lipase A "Amano" 6 (made by Amano Seiyaku K.K.) was dissolved in 98.32 parts by weight of hardened tallow. The mixture in an amount of 35.8 parts by weight per 100 parts by weight of the cores screened to a diameter of 1.5 mm on the average was coated on the cores. Then, 7.2 parts by weight, per 100 parts by weight of the cores, of hardened tallow which had been molten. The resulting coated particles were subjected to the above-mentioned evaluation test. Consequently, the elution into a rumen was 9%, and the corresponding elution into digestive organs was 76%.

Production Example 2

Production Example of rumen-bypass amino acid:

L-lysine hydrochloride (616 g), 196 g of methionine, 525 g of alanine, 525 g of glutamine, 172.5 g of talc, 2.5 g of sodium carboxymethylcellulose and 135 g of water were charged into a kneader, and kneaded. The mixture was formed into cylindrical granules using an extrusion-pulverizer having a screen with 1.5 mm φ openings. The shape of the thus-obtained granules was adjusted using a device for forming spherical granules (Malmerizer, supplied by Fuji Paudal) to obtain nearly spherical granules. The resulting spherical granules were subjected to fluidized drying to give cores containing L-lysine hydrochloride and having a diameter distribution of from 1 mm to 2.5 mm.

A protective substance containing 1.68 parts by weight of lipase A "Amano" 6 (made by Amano Seiyaku K. K.) was dissolved in 98.32 parts by weight of hardened tallow. The mixture in an amount of 35.8 parts by weight per 100 parts by weight of the cores screened to a diameter of 1.5 mm on the average was coated on the cores. Then, 7.2 parts by weight, per 100 parts by weight of the cores, of hardened tallow which had been molten were coated thereon. The resulting coated particles were subjected to the above-mentioned evaluation test. Consequently, the elution into a lumen was 9%, and the corresponding elution into digestive organs was 72%.

Example 1

Thirty Holstein secundipara dairy cows (amount of milk produced—10,000 kg/head/year, scheduled intake of a feed calculated in terms of a dry matter—24 kg/day) were divided into two groups, namely 15 cows in a protein supply area (positive control area) and 15 cows in a rumen-bypass amino acid supply area (RPAA supply area). In the dry period before calving, the dry period formula feed shown in Table 1 was administered to dairy cows in the protein supply area from 3 weeks before calving to the calving day. In the RPAA supply area, the dry period formula feed shown in Table 1 was administered thereto from 3 days before the scheduled calving day. Subsequently, in the lactation period, the lactation period formula feed shown in Table 2 was administered thereto. The amino acid balance of the rumen-bypass amino acid (RPAA) supply feed in the dry period is shown in Table 3, the amino acid balance of the protein supply feed in the dry period in Table 4, the amino acid balance of the lysine-methionine-deficient feed and the rumen-bypass amino acid supply feed in the lactation period in Table 5, and the amino acid balance of the protein supply feed in the lactation period in Table 6 respectively. The rumen-bypass amino acid obtained in Production Example 2 was administered to dairy cows in the RPAA supply area in amounts shown in Tables 1 and 2. With respect to the breeding records, the intake of the feed calculated in terms of a dry matter is shown in Table 7. The health conditions and the fatness of dairy cows were visually estimated according to the 5-grade method, and the scores are shown in Table 8. The blood was sampled from all of dairy cows in both of the protein supply area and the RPAA supply area on Day 14 before scheduled calving and on Day 14 and Day 56 after calving. Then, the blood glucose value and the blood urea nitrogen (BUN) value were measured. The results are shown in Table 9.

TABLE 1

Dry period formula feed

|  | Rumen-bypass amino acid supply feed | | Protein supply feed*1 | |
| --- | --- | --- | --- | --- |
|  | Amount of a dry matter (%) | Dairy cow intake (Lbs/day), calculated as a dry matter | Amount of a dry matter (%) | Dairy cow intake (Lbs/day), calculated as a dry matter |
| Soybean cake | 0.73 | 0.18 | 1.43 | 0.38 |
| Grass silage | 36.70 | 10.00 | 40.00 | 10.00 |
| By-pass fat | 0.73 | 0.18 | 0.72 | 0.18 |
| Corn fermentation cake | 3.88 | 0.98 | 0.48 | 0.12 |
| Corn | 4.84 | 1.22 | 5.64 | 1.41 |
| Barley | 4.84 | 1.22 | 5.96 | 1.49 |
| Vitamin• mineral | 0.83 | 0.21 | 0.71 | 0.18 |
| Hay (oats) | 36.70 | 10.00 | 40.00 | 10.00 |
| High-water-content corn | 3.97 | 1.00 | 4.00 | 1.00 |
| By-pass amino acid | 0.78 | 0.20 | — | — |
| Meat meal with bone | — | — | 0.48 | 0.12 |
| Blood meal | — | — | 0.34 | 0.08 |
| Fish meal | — | — | 0.24 | 0.06 |

*1Crude protein content (calculated as a dry matter) 14.8%

TABLE 2

Dry period formula feed

|  | Rumen-bypass amino acid supply feed | | Protein supply feed | |
| --- | --- | --- | --- | --- |
|  | Amount of a dry matter (%) | Dairy cow intake (Lbs/day), calculated as a dry matter | Amount of a dry matter (%) | Dairy cow intake (Lbs/day), calculated as a dry matter |
| Soybean cake (Crude protein 49%) | 2.81 | 1.50 | 5.81 | 3.00 |
| Grass silage | 32.13 | 17.50 | 31.78 | 17.00 |
| By-pass fat | 2.80 | 1.50 | 2.80 | 1.50 |
| Corn fermentation cake | 15.01 | 8.00 | 1.87 | 1.00 |
| Corn | 18.78 | 10.00 | 22.08 | 11.80 |
| Barly | 18.78 | 10.00 | 23.36 | 12.50 |
| Vitamin• mineral | 3.32 | 1.77 | 5.61 | 3.00 |
| Hay (Alfalfa) | 5.64 | 3.00 | 2.80 | 1.50 |
| By-pass amino acid | 0.74 | 0.40 | — | — |
| Meat meal with bone | — | — | 1.87 | 1.00 |
| Blood meal | — | — | 1.31 | 0.70 |
| Fish meal | — | — | 0.93 | 0.50 |

*1Crude protein content (calculated as a dry matter) 18.6%

TABLE 3

|  | A Feed amino acid g/day | B Small intestine absorption amount g/day | C Amino acid demand g/day | D Excess amount, RPAA supply (%) |
| --- | --- | --- | --- | --- |
| Methionine | 29.5 | 22.2 | 15.7 | 169 |
| Lysine | 84.1 | 88.7 | 40.0 | 174 |
| Arginine | 72.6 | 60.1 | 45.3 | 151 |
| Threonine | 50.3 | 49.5 | 30.0 | 185 |
| Leucine | 97.9 | 77.8 | 48.0 | 157 |
| Isoleucine | 74.0 | 51.9 | 29.4 | 178 |
| Valine | 29.9 | 58.5 | 34.3 | 171 |
| Histidine | 53.8 | 24.1 | 15.6 | 155 |
| Phenylalanine | 83.8 | 50.0 | 27.1 | 194 |
| Tryptophan | 18.0 | 11.3 | 7.4 | 153 |

TABLE 4

|  | A Feed amino acid g/day | B Small intestine absorption amount g/day | C Amino acid demand g/day | D Excess amount, (B/C) (%) |
| --- | --- | --- | --- | --- |
| Methionine | 30.2 | 23.0 | 15.7 | 147 |
| Lysine | 89.1 | 62.8 | 40.0 | 157 |
| Arginine | 78.1 | 63.9 | 45.3 | 141 |
| Threonine | 62.2 | 51.6 | 30.0 | 172 |
| Leucine | 100.8 | 81.1 | 48.0 | 169 |
| Isoleucine | 66.2 | 53.8 | 29.4 | 183 |
| Valine | 76.4 | 61.4 | 34.3 | 179 |
| Histidine | 31.7 | 26.2 | 15.6 | 168 |
| Phenylalanine | 66.3 | 52.6 | 27.1 | 194 |
| Tryptophan | 16.2 | 11.3 | 7.4 | NA |

TABLE 5

|  | A Feed amino acid g/day | B Small intestine absorption amount g/day | C Amino acid demand g/day | D Excess amount, RPAA administration area (%) |
| --- | --- | --- | --- | --- |
| Methionine | 88.8 | 52.0 | 58.3 | 110 |
| Lysine | 186.8 | 150.3 | 178.8 | 110 |
| Arginine | 177.2 | 150.0 | 106.2 | 143 |
| Threonine | 142.2 | 119.6 | 100.5 | 118 |
| Leucine | 259.9 | 216.7 | 183.3 | 118 |
| Isoleucine | 152.5 | 125.7 | 142.9 | 110 |
| Valine | 182.2 | 149.5 | 140.2 | 113 |
| Histidine | 75.8 | 83.6 | 81.7 | 115 |
| Phenylalanine | 159.8 | 130.3 | 102.0 | 128 |
| Tryptophan | 32.0 | 22.6 | 35.8 | NA |

TABLE 6

|  | A Feed amino acid g/day | B Small intestine absorption amount g/day | C Amino acid demand g/day | D Excess amount, (B/C) (%) |
| --- | --- | --- | --- | --- |
| Methionine | 72.2 | 59.5 | 58.3 | 102 |
| Lysine | 234.0 | 198.5 | 178.8 | 111 |
| Arginine | 211.7 | 190.1 | 106.2 | 179 |
| Threonine | 160.6 | 139.7 | 100.5 | 139 |
| Leucine | 289.3 | 247.5 | 183.3 | 135 |
| Isoleucine | 167.6 | 141.5 | 142.9 | 99 |
| Valine | 206.9 | 174.1 | 140.4 | 124 |

TABLE 6-continued

| | A<br>Feed<br>amino<br>acid<br>g/day | B<br>Small intest-<br>ine absorp-<br>tion amount<br>g/day | C<br>Amino acid<br>demand<br>g/day | D<br>Excess<br>amount,<br>(B/C)<br>(%) |
|---|---|---|---|---|
| Histidine | 94.1 | 107.8 | 81.7 | 132 |
| Phenylalanine | 183.2 | 155.0 | 102.0 | 152 |
| Tryptophan | 34.4 | 24.3 | 35.8 | NA |

TABLE 7

Dry matter intake (DMI) in a feed in Tables 14 and 15 (Kg/day)

| | before calving | | | after calving | | | |
|---|---|---|---|---|---|---|---|
| | 3 weeks | 2 weeks | 1 week | 2 weeks | 4 weeks | 6 weeks | 8 weeks |
| Protein supply area | 13.1 | 10.4 | 9.0 | 14.3 | 17.0 | 17.4 | 17.0 |
| Rumen-bypass Amino acid administration area | 12.9 | 10.2 | 8.4 | 13.3 | 16.1 | 21.2 | 21.0 |

Holstein cows (15 head/area); secundipara or multipara, amount of milk produced –10,000 kg/head/year, feed amount - 24 kg (calculated as a dry matter)

TABLE 8

Body condition score (BCS) of dairy cows bred

| | before calving | | | after calving | | | |
|---|---|---|---|---|---|---|---|
| | 3 weeks | 2 weeks | 1 week | 2 weeks | 4 weeks | 6 weeks | 8 weeks |
| Protein supply area | 4.1 | 4.0 | 3.8 | 3.2 | 2.5 | 2.2 | 2.5 |
| Rumen-bypass Amino acid administration area | 4.0 | 4.0 | 4.0 | 3.4 | 2.8 | 2.6 | 2.5 |

TABLE 9

| | Blood glucose value (mg/dl) | | Blood urea nitrogen (BUN) value (mg/dl) | |
|---|---|---|---|---|
| | Protein supply area | RPAA supply area | Protein supply area | RPAA supply area |
| Day 14 before calving | 51 | 52 | 13.2 | 11.3 |
| Day 15 after calving | 36 | 47 | 12 2 | 9.1 |
| Day 56 after calving | 49 | 70 | 13.5 | 12.6 |

Example 2

Forty Holstein secundipara or multipara cows were divided into two groups, and subjected to a test. The dry period complete mixed feed shown in Table 10 was administered to 20 cows in the control area and 20 cows in the rumen-bypass amino acid administration area (RPAA administration area) from 3 weeks before calving to the calving day. Further, the rumen-bypass amino acid obtained in Production Example 2 was administered to the cows from 3 days before the scheduled calving day. After calving, the lactation period complete mixed feed shown in Table 11 (the amino acid composition is shown in Tables 12 and 13) was supplied to the control area and the rumen-bypass amino acid administration area. In the RPAA administration area, it was continuously administered for 8 weeks after calving. With respect to the total of 40 cows in both areas, the number of days of the first estrus after calving, the non-conception rate, and the number of matings until the conception are shown in Tables 14 to 16. The control area was compared with the rumen-bypass amino acid administration area. As a result, regarding the number of days of estrus after calving, the rate of the first estrus which was reached within 100 days was 78% in the control area, whereas it was 89% in the RPAA administration area. Regarding the number of matings until the conception, the rate of conception by one mating was 33% and the rate of conception by three or more matings was 39% in the control area. Meanwhile, the rate of conception by one mating was 55%, and all of dairy cows were conceived by at most two matings in the RPAA administration area. Thus, the conception occurred at good efficiency. Accordingly, the rate of the non-conception was naturally decreased. On the other hand, in the RPAA administration area as compared to the control area, the rate of non-conception within 80 days was 55% relative to 22%, and that within 120 days was 100% relative to 58%; it was thus improved. It is presumably because the RPAA administration improved the energy balance and activated the liver function of dairy cows, maintaining the good conditions of dairy cows, increasing their bodily strength, and releasing the stress.

TABLE 10

| Dry period complete formula feed | Intake of dairy cows (Lbs/day) | Dry matter composition (%) |
|---|---|---|
| Corn silage | 7:00 | 29:4 |
| High-water-content corn | 4:50 | 18:9 |
| Beer cake | 1:84 | 7:7 |
| Soybean flour 49 (m) | 1:03 | 4:3 |
| Corn gluten meal (m) | 0:10 | 0:4 |
| Safflower meal (m) | 0:06 | 0:3 |
| Wheat flour (m) | 0:19 | 0:8 |
| Mineral•vitamin | 0:67 | 2:8 |
| Grass silage 934 | 7:20 | 30:2 |
| Corn fermentation cake | 0:47 | 2:0 |
| Blood meal (m) | 0:68 | 2:8 |
| Feather meal blend (m) | 0:06 | 0:3 |
| Urea (m) | 0:03 | 0:1 |
| Total (m) | 28:83 | 100:0 |

TABLE 11

| | Control area | | RPAA administration area | |
|---|---|---|---|---|
| Lactation period feed | Dry matter intake (Lbs/day) | Mixing ratio (%) | Dry matter intake (Lbs/day) | Mixing ratio (%) |
| Wheat flour (m) | 4:45 | 7:8 | 4:45 | 7:7 |
| Soybean cake (m) | 3:38 | 5:9 | 3:38 | 5:8 |
| Cane molasses | 0:23 | 0:4 | 0:23 | 0:4 |
| Mineral•vitamin | 1:61 | 2:8 | 1:61 | 2:8 |
| Corn silage 40% | 12:31 | 21:6 | 12:31 | 21:3 |
| Dry corn flour 68 | 13:93 | 24:5 | 13:93 | 24:1 |
| Corn dist | 4:80 | 8:4 | 4:80 | 8:3 |
| Corn gluten meal | 0:68 | 1:2 | 0:68 | 1:2 |
| Blood meal | 0:88 | 1:6 | 0:88 | 1:6 |
| Hardened tallow | 0:30 | 0:5 | 0:30 | 0:5 |
| Safflower meal | 3:81 | 6:7 | 3:81 | 6:8 |
| Alfalfa hay | 7:63 | 13:4 | 7:63 | 13:2 |
| Feather flour | 1:40 | 2:6 | 1:40 | 2:4 |
| Bone with meal | 9:36 | 0:6 | 0:36 | 0:6 |
| Fat | 1:11 | 2:0 | 1:11 | 1:9 |
| RPAA | — | — | 0:98 | 1:7 |
| Total | 58:88 | 100:9 | 57:88 | 100:0 |

TABLE 12

Lactation period feed amino acid balance (control area)

| | A Feed amount (g/day) | B Small intestine absorption amount (g/day) | C Demand (g/day) | D (B/C) Supply ratio (%) |
|---|---|---|---|---|
| Methionine | 70:1 | 58:5 | 64:5 | 87 |
| Lysine | 224:4 | 188:9 | 198:5 | 95 |
| Arginine | 230:1 | 201:6 | 112:5 | 179 |
| Threonine | 170:1 | 147:3 | 109:8 | 134 |
| Leucine | 333:5 | 290:0 | 204:9 | 142 |
| Isoleucine | 174:1 | 148:3 | 180:2 | 93 |
| Valine | 236:5 | 202:3 | 158:2 | 130 |
| Histidine | 100:5 | 87:7 | 68:7 | 128 |
| Phenylalanine | 198:8 | 167:8 | 112:4 | 148 |
| Tryptophan | 28:5 | 20:1 | 39:8 | — |

TABLE 13

Lactation period feed amino acid balance (control area)

| | A Feed amount (g/day) | B Small intestine absorption amount (g/day) | C Demand (g/day) | D (B/C) Supply ratio (%) |
|---|---|---|---|---|
| Methionine | 82:7 | 59:2 | 65:0 | 105 |
| Lysine | 285:1 | 229:9 | 199:9 | 115 |
| Arginine | 228:7 | 201:3 | 119:7 | 177 |
| Threonine | 169:7 | 147:0 | 110:8 | 133 |
| Leucine | 333:2 | 290:0 | 206:2 | 141 |
| Isoleucine | 173:6 | 148:3 | 161:1 | 92 |
| Valine | 236:1 | 202:1 | 157:2 | 129 |
| Histidine | 100:4 | 87:7 | 68:2 | 127 |
| Phenylalanine | 198:4 | 167:4 | 113:3 | 148 |
| Tryptophan | 28:2 | 19:9 | 40:1 | — |

TABLE 14

Total rate of estrus which was reached after calving (%)

| | within 60 days | within 80 days | within 100 days | 100 days or more |
|---|---|---|---|---|
| Control area | 47 | 68 | 78 | 100 |
| RPAA administration area | 47 | 68 | 89 | 100 |

TABLE 15

Total rate of mating success (%)

| | 1st | 2nd | 3rd | 4th |
|---|---|---|---|---|
| RPAA administration area | 33 | 41 | 68 | 100 |
| Control area | 55 | 100 | — | — |

TABLE 16

Total rate of non-conception after calving (%)

| | within 80 days | within 100 days | within 120 days | within 160 days |
|---|---|---|---|---|
| Control area | 78 | 67 | 55 | 0 |
| RPAA administration area | 45 | 18 | 0 | — |

Effects of the Invention

Lysine and methionine which are limiting amino acids of dairy cows are administered to dairy cows to decrease the BUN value that has an adverse effect on the conception rate and to increase the blood glucose required to improve the energy balance, that alanine and glutamine are administered to dairy cows to increase the blood glucose and to improve the liver function, and that the use of these amino acids is effective for keeping good conditions of dairy cows, allowing earlier arrival of initial estrus without any stress, improving the mating conception rate and decreasing the non-conception rate.

What is claimed is:
1. A method of increasing fertility in high-level lactation dairy cows, which method comprises controlling the daily continuous administration of a feed additive in the cows' diet; said feed additive being selected from the group consisting of
a rumen-protected mixture of lysine, glutamine and alanine;

a rumen-protected mixture of lysine and glutamine; and a rumen-protected mixture of lysine and alanine;

wherein the daily continuous administration of the feed additive begins approximately 3 days before calving and ends approximately 84 days after calving;

wherein the increase in fertility is manifested as a member selected from the group consisting of an increase in conception rate;

a decrease in non-conception rate; and an early arrival of initial estrus as compared to high-level lactation dairy cows which do not receive the rumen-protected feed additive;

and wherein the energy balance of the cows is always plus and the amino acid demand of the cows is satisfied.

2. A method according to claim 1 wherein the feed additive further comprises methionine.

3. A method according to claim 1 wherein the increase in fertility is manifested as an increase in conception rate.

4. A method according to claim 1 wherein the increase in fertility is manifested as a decrease in non-conception rate.

5. A method according to claim 1 wherein the increase in fertility is manifested as an early arrival of initial estrus as compared to high-level lactation dairy cows which do not receive the rumen-protected feed additive.

6. A method according to claim 1 wherein during said administration period of the feed additive the BUN value of the cow is decreased and the blood glucose of the cow is increased relative to a cow which does not receive the feed additive.

7. A method of increasing fertility in high-level lactation dairy cows, which method comprises controlling the daily continuous administration of a feed additive in the cows' diet; said feed additive being selected from the group consisting of a rumen-protected mixture of lysine, glutamine and alanine;

a rumen-protected mixture of lysine and glutamine; and a rumen-protected mixture of lysine and alanine;

wherein the daily continuous administration of the feed additive begins approximately 21 day before calving and ends approximately 84 days after calving;

wherein the increase in fertility is manifested as a member selected from the group consisting of an increase in conception rate;

a decrease in non-conception rate; and an early arrival of initial estrus as compared to high-level lactation dairy cows which do not receive the rumen-protected feed additive;

and wherein the energy balance of the cows is always plus and the amino acid demand of the cows is satisfied.

8. A method according to claim 7 wherein the feed additive further comprises methionine.

9. A method according to claim 7 wherein the increase in fertility is manifested as an increase in conception rate.

10. A method according to claim 7 wherein the increase in fertility is manifested as a decrease in non-conception rate.

11. A method according to claim 7 wherein the increase in fertility is manifested as an early arrival of initial estrus as compared to high-level lactation dairy cows which do not receive the rumen-protected feed additive.

12. A method according to claim 7 wherein during said administration period of the feed additive the BUN value of the cow is decreased and the blood glucose of the cow is increased relative to a cow which does not receive the feed additive.

* * * * *